United States Patent [19]
Thomas et al.

[11] Patent Number: 6,037,118
[45] Date of Patent: Mar. 14, 2000

[54] VIRAL CHARACTERIZATION BY DIRECT DETECTION OF CAPSID PROTEINS

[75] Inventors: John J. Thomas; Catherine Fenselau, both of Baltimore, Md.

[73] Assignee: University of Maryland Baltimore County, Baltimore, Md.

[21] Appl. No.: 09/120,861

[22] Filed: Jul. 22, 1998

Related U.S. Application Data

[60] Provisional application No. 60/085,389, May 14, 1998.

[51] Int. Cl.[7] .............................. C12Q 1/70; G01N 1/28; G01N 37/00
[52] U.S. Cl. ................................................ 435/5; 250/282
[58] Field of Search .................................. 435/5; 250/282

[56] References Cited

PUBLICATIONS

Siuzdak, G. Journal of Mass Spectrometry 33:203–211, 1998.
Krishnamurthy et al. Journal of Natural Toxins 6:121–162, Jun. 1997.

*Primary Examiner*—Mary E. Mosher
*Attorney, Agent, or Firm*—Benjamin Aaron Adler

[57] ABSTRACT

The present invention provides a method of direct detecting of capsid proteins from intact viral particles using matrix-assisted laser desorption/ionization (MALDI) time-of-flight mass spectrometry, which enables viral proteins to be characterized at the femtomolar level in complex biological milieu with minimal or no cleanup.

9 Claims, 6 Drawing Sheets nucleocapsid protein monomers coat protein monomers

VIRAL CHARACTERIZATION BY DIRECT DETECTION OF CAPSID PROTEINS

CROSS-REFERENCE TO RELATED APPLICATION

This non-provisional patent application claims benefit of provisional patent application U.S. Ser. No. 60/085,389, filed May 14, 1998, now abandoned.

BACKGROUND OF THE INVENTION

1. Field of the Invention

The present invention relates generally to the fields of analytical chemistry and biochemistry. More specifically, the present invention relates to direct viral characterization by mass spectrometric detection of capsid proteins.

2. Description of the Related Art

Medical, agricultural, and military personnel who need to monitor and identify microbial agents often utilize enzyme-linked immunosorbent assays, serological, morphological, and other microbiological methods (1). Certain viruses represent a biological threat; therefore, a need exists for rapid detection of characteristic viral biomarkers. Field responses to biological agents require completion of the entire analysis in less than 10 minutes, thereby leaving only minutes for chemical manipulation of the sample.

Since the inception of matrix-assisted laser desorption ionization (MALDI) mass spectrometry (2), the marriage of this desorption/ionization technique with time-of-flight mass spectrometers has enabled scientists to detect large biopolymers with high sensitivity (3). Semi-purified mixtures of proteins have been analyzed with matrix-assisted laser desorption ionization mass spectrometry in the past, thereby providing a more accurate alternative to the commonly used SDS/PAGE analysis of protein mixtures (4). The energy imparted from matrix-assisted laser desorption ionization onto proteins and the conformationally indiscriminate time-of-flight removes some effects of complex protein solution behavior, which can alter the gel migration of different proteins. Mass spectrometry also provides mass measurements in a shorter amount of time than electrophoresis.

Viruses and bacteriophages contain large quantities of proteins, which perform various functions for each virion. One type of protein commonly found in viruses, which is known as a nucleocapsid or coat protein, encapsulates nucleic acid molecules at the core of the organism. In certain more complex virions, this protein capsid layer is surrounded by a lipoglycoprotein layer. The viruses in this study consist of a defined number of homogeneous capsid protein molecules in close association with the viral nucleic acids. FIG. 1 displays the structures of the MS2, tobacco mosaic (TMV) and Venezuelan equine encephalitis (VEE) viruses.

TMV and the MS2 bacteriophage are representative of an RNA virus and bacteriophage respectively. Despite different protein conformations and resulting structural organization, these proteins perform similar functions of acting as translational repressors of the phage-encoded replicase gene, protecting the viral RNA, and serving as a nucleation site for viral assembly. The icosadeltahedron shaped MS2 bacteriophage consist of 180 copies of a coat protein with a molecular weight of 13,730 Da surrounding a single stranded RNA, and one copy of an "A-protein" (MW ~44 kDa). The TMV virus is a spherical virus consisting solely of coat proteins, which has species dependent molecular weights of 17,100–17,600 Da.

Venezuelan equine encephalitis was used as an example of membrane-containing viruses, which are assembled by interaction of viral proteins with the host cell membrane. Venezuelan equine encephalitis contains a single stranded RNA genome encapsulated by 240 copies of a nucleocapsid protein (M.W. 30,940 Da) surrounded by a lipid bilayer containing two glycoproteins, E1 and E2 that have molecular masses of ~50,000 and ~56,000 Da, respectively (5–7). While the relative abundance of these unique biomarkers presents an opportunity for identification of the virus, scientists have only recently attempted to rapidly identify these biomarkers. Previously, mass spectrometric detection of viral coat proteins required extensive off-line or elaborate on-line cleanup processes. Despeyroux et al. utilized HPLC on-line with electrospray mass spectrometry to determine molecular weights of specific capsid proteins (8).

The prior art is deficient in the lack of effective means of identifying viruses from completely crude biological media with minimal or no cleanup. Further, the prior art is deficient in the lack of effective means for rapid detection of as little as femtomoles of coat protein within a complex biological medium. The present invention fulfills this long-standing need and desire in the art.

SUMMARY OF THE INVENTION

Matrix-assisted laser desorption ionization (MALDI) mass spectrometry has enabled detection of viral proteins with minimal separation from crude biological media. This analysis has been achieved with a combination of organic acids and high energy desorption with a nitrogen laser. The molecular weights from these proteins are sufficiently unique to differentiate among species of viruses in a variety of biological conditions. This analysis has provided the means for rapid detection of as little as femtomoles of coat protein within a complex biological medium.

In one embodiment of the present invention, there is provided a method of detecting viral structural proteins rapidly and directly from a complex environment by utilizing mass spectrometry with the addition of specific organic acids.

In a preferred embodiment, the organic acid is acetic acid or citric acid, and premixed with mass spectrometry matrix. A representative viral protein is a capsid protein. Preferably, the semi-purified or non-purified sample is prepared from the complex environment.

Representative examples of mass spectrometry are fast atom bombardment mass spectrometry, plasma desorption mass spectrometry, laser desorption mass spectrometry, matrix-assisted laser desorption ionization time-of-flight mass spectrometry and electrospray mass spectrometry, wherein the laser is of any kind and has wavelength of any range. Preferably, the method detects femtomolar concentration of the viral protein in less than 3 minutes. The method also detects bacteriophage proteins.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the structure of bacteriophage and virus.

DETAILED DESCRIPTION OF THE INVENTION

Figure 1B:
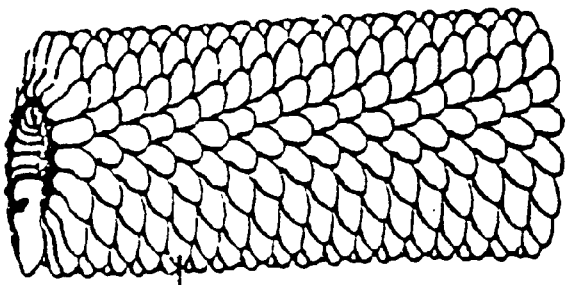
FIG. 1B shows tobacco mosaic virus.
Figure 1C:
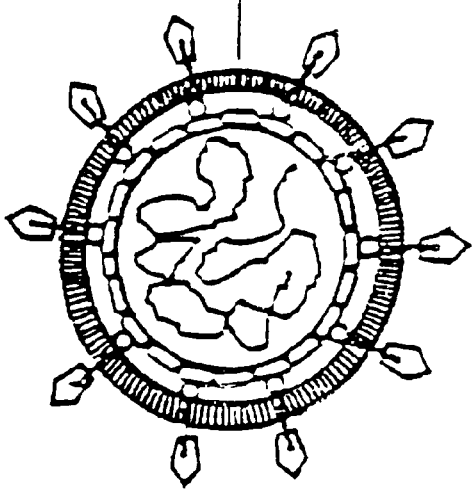
FIG. 1C shows Venezuelan equine encephalitis virus.
Figure 1A:
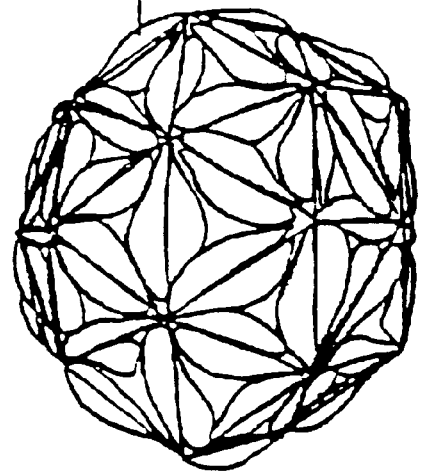
FIG. 1A shows MS2 bacteriophage.

In the present invention, a method of rapid detecting of viral proteins from a complex medium is disclosed, comprising the steps of preparing a crude sample of the medium; mixing the sample with an organic acid; and detecting viral characteristic structural proteins by utilizing mass spectrometry. As used herein, "crude sample" refers to the unadulterated growth medium which may contain salts, buffers, peptides, lipids, oligonucleotides, sugars and other chemicals. Certain organic acids will be useful in this technique as will be readily recognized by a person having ordinary skill in this art based on the disclosure herein. Preferably, the organic acid is acetic acid or citric acid, and premixed with mass spectrometry matrix. The crude sample is either semi-purified or non-purified preparation and may contain only femtomolar levels of viral proteins. In a preferred embodiment, the viral protein is a capsid protein. Representative examples of mass spectrometry are fast atom bombardment mass spectrometry, plasma desorption mass spectrometry, laser desorption mass spectrometry, matrix-assisted laser desorption ionization time-of-flight mass spectrometry and electrospray mass spectrometry, wherein the laser is of any kind and has wavelength of any range. In a preferred embodiment, the method detects femtomolar concentration of the viral protein in less than 3 minutes. The method may also detect bacteriophage proteins.

The following examples are given for the purpose of illustrating various embodiments of the invention and are not meant to limit the present invention in any fashion.

EXAMPLE 1
Equipment and Chemicals

MALDI spectra were taken on a Kratos/Shimadzu Kompact MALDI III ™ (Manchester, U. K.) in linear mode. Matrix-assisted laser desorption ionization was attained with a nitrogen laser ($\lambda$=337 nm) and an acceleration voltage of 20 kV. Samples were desorbed from stainless steel plates with preconstructed sample wells. All protein standards and matrices were purchased from Sigma Chemical Co. (St. Louis, Mo.) and used as received. HPLC-grade solvents were purchased from Fisher Scientific, Inc. (Pittsburgh, Pa.).

EXAMPLE 2
Biological Growth Conditions

A host culture of an Hfr strain (i.e. male specific) of E.coli (ATCC 15669; Rockville, Md.) was grown for 16 hours at 37° C. in MS2 broth, and was then used to inoculate a larger culture (9). Bacteriophage stock suspension was added to the bacterial culture when the culture reached 1 08 cfu/ml as determined with a Gilford RESPONSE™ dual channel UV-spectrophotometer (Gilford Instruments; Oberlin, Ohio). The phage culture was incubated at 37° C. for 2–3 hours.

Homogenates of ground tobacco leaf samples (ATCC PV-635) in 50 mM phosphate buffer (pH 7.5) were used to propagate tobacco mild green mosaic virus (U2 strain) onto healthy young tobacco plants. The plants were inoculated by causing microscopic abrasions with a throat-powder spray of carborundum before applying the sap homogenate by hand (10). The infected plants were sustained under incandescent/UV light for 2 weeks before harvest. All materials in contact with TMV were sterilized after use.

Venezuelan equine encephalitis Trinidad donkey virus (VEE-TRD) 3000 strain was expressed from cDNA, and propagated in baby hamster kidney cells. The growth media was composed of EMEM supplemented with 5% fetal bovine serum. The collected virus was precipitated with polyethylene glycol and salt. The precipitate was resuspended in phosphate buffer saline and layered onto a sucrose gradient. The semi-purified virus was irradiated with $Co^{60}$ for safe handling.

EXAMPLE 3

Analytical Methods

Crude MS2, as well as VEE preparations with 50% (v/v) organic acid were applied directly to the stainless steel MALDI slide with a small volume metal tip syringe, and sandwiched by the matrix (11). Crude TMV samples were analyzed by cleanly cutting strips of infected leaves, and strategically placing them on stainless steel slides with one-sided tape. The leaf slices were treated with 0.3 μl of organic acid 15–30 seconds before adding 2×0.3 μl of matrix. Semi-purified preparations of MS2/*E. Coli* and TMV were processed by pelleting bacteria and plant cell debris with high speed centrifugation, and the supernatant containing the virus was partially purified by centrifugation-filtration (Ultrafree filters, Millipore Corp., Bedford, Mass.).

External calibrations were executed with chicken lysozyme (M.W. 14,307), bovine trypsinogen (M.W. 23,957), and bovine serum albumin (M.W. 66,431) for MS2, TMV, and VEE-TRD analysis, respectively. In order to avoid spatial source effects, calibration for crude TMV analysis was performed by applying the calibrant and matrix to a separate piece of tobacco leaf.

EXAMPLE 4

Results

Detection, mass accuracy, and mass resolution of viral proteins with matrix-assisted laser desorption ionization are dependent on sample preparation and complexity, as well as mass spectrometric conditions. Capsid proteins often contain hydrophobic regions that maintain the protein-protein associations. These hydrophobic regions contribute to the nucleocapsid or coat structure, and cause aggregation in aqueous solution. Despite a high percentage of organic content in the matrix solvent, no signal was observed from virus sample and matrix alone.

EXAMPLE 5
Detection of MS2 Bacteriophage

The growth conditions for MS2 yield numerous amounts of biomolecules released from lysed host bacterial cells. In addition, the optimal broth contains large quantities of salts, peptides, and proteins, which potentially suppress the signal of interest in the matrix-assisted laser desorption ionization spectrum. Considering the MS2 phage culture had an active concentration of $2.1 \times 10^{10}$ pfu/ml, which translates to a minimum 1 femtomole of coat protein applied to the slide well, any signal suppression could lead to no observed peak of interest. No signal was observed with prior application of nitrocellulose, PVDF membranes, or C8 membranes with and without washing. Such surfaces sometimes have higher laser intensity thresholds for desorption of ions (12).

The dissociation of viral proteins have historically been accomplished with urea (13, 14), acetic acid (15) or detergents (16, 17). Careful selection of matrix additives is necessary due to signal suppression caused by the acidity/basicity, crystallization, and desorption properties of he additives (12, 18).

Figure 2A:
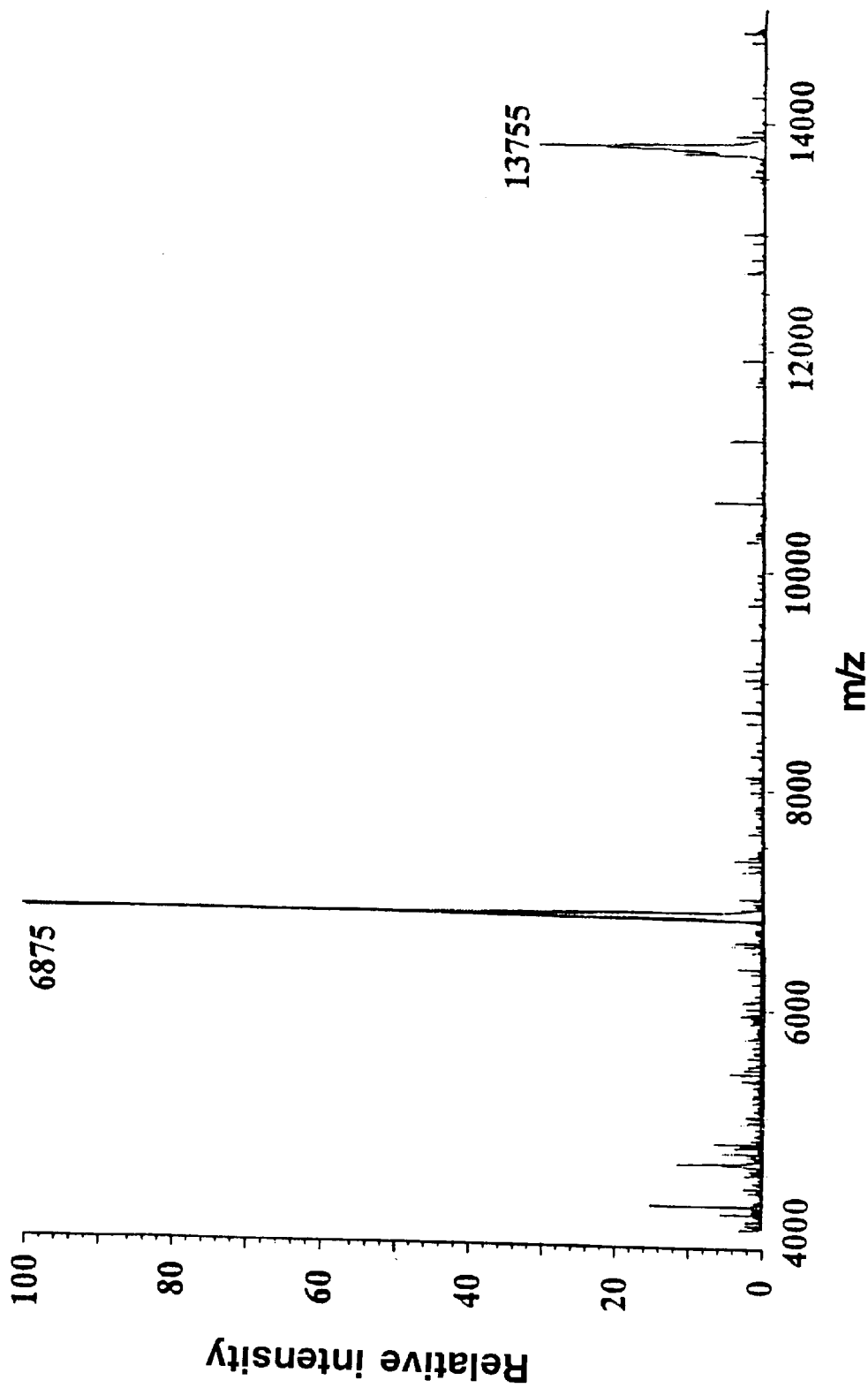
FIG. 2 shows the matrix-assisted laser desorption ionization mass spectra of semi-purified MS2 bacteriophage with acetic acid (FIG. 2A), and citric acid (FIG. 2B) with α-cyano-4-hydroxycinnamic acid matrix.
Figure 2B:
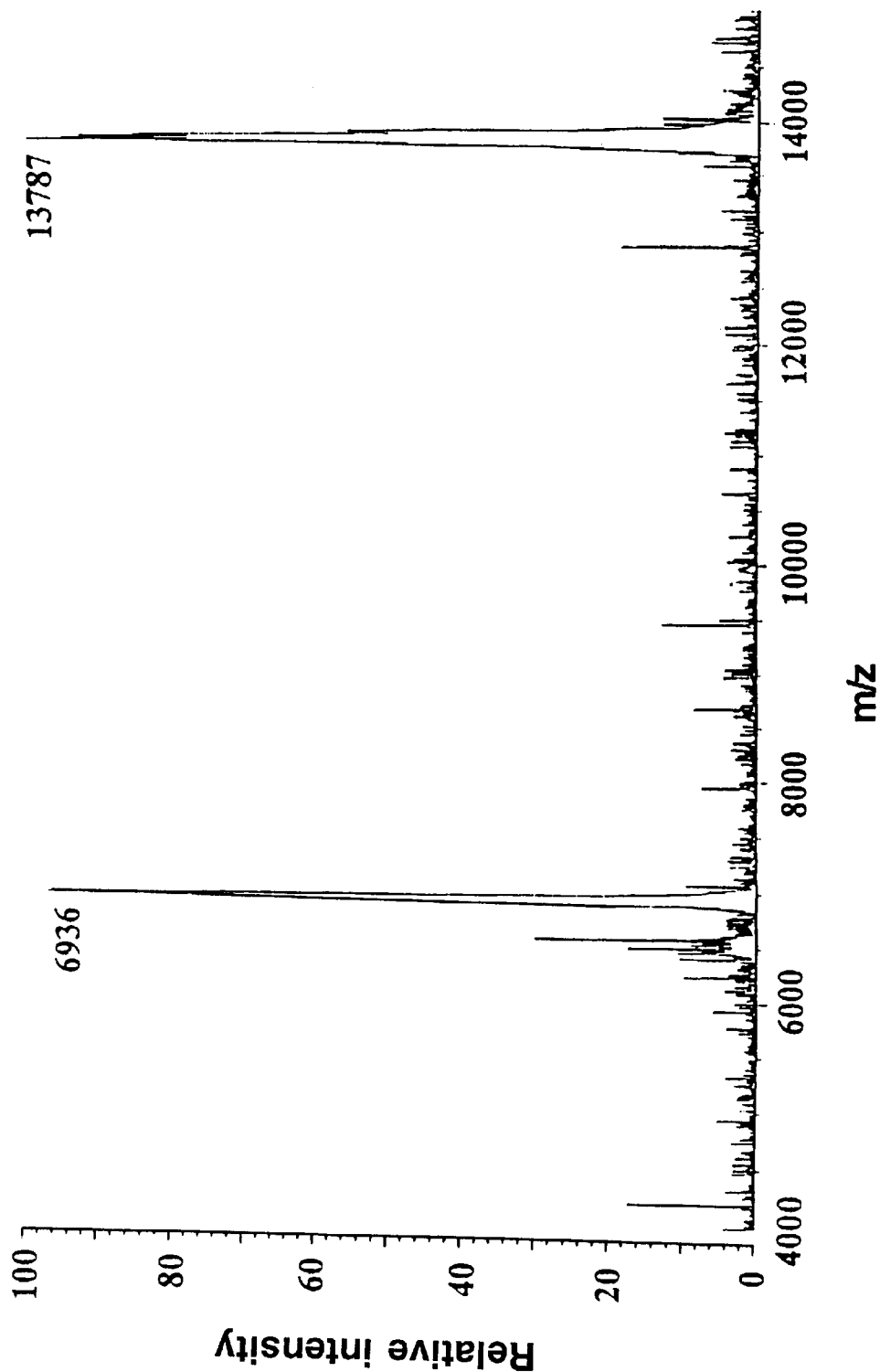

FIG. 2 demonstrates differences observed in matrix-assisted laser desorption ionization spectra of semi-purified preparations of a MS2 culture, which independently had acetic and citric acid added to the solution. Citric acid yielded better mass accuracy, and mass resolution, but more doubly charged ions with approximately the same laser intensity. Citric acid has three acidic protons: one with a pKa lower than the single acidic proton of acetic acid, and another equal to the acidic proton of acetic acid. Sodium citrate has been shown to enhance MALDI protein spectra from buffered protein solutions laden with salts (19, 20).

Figure 3:
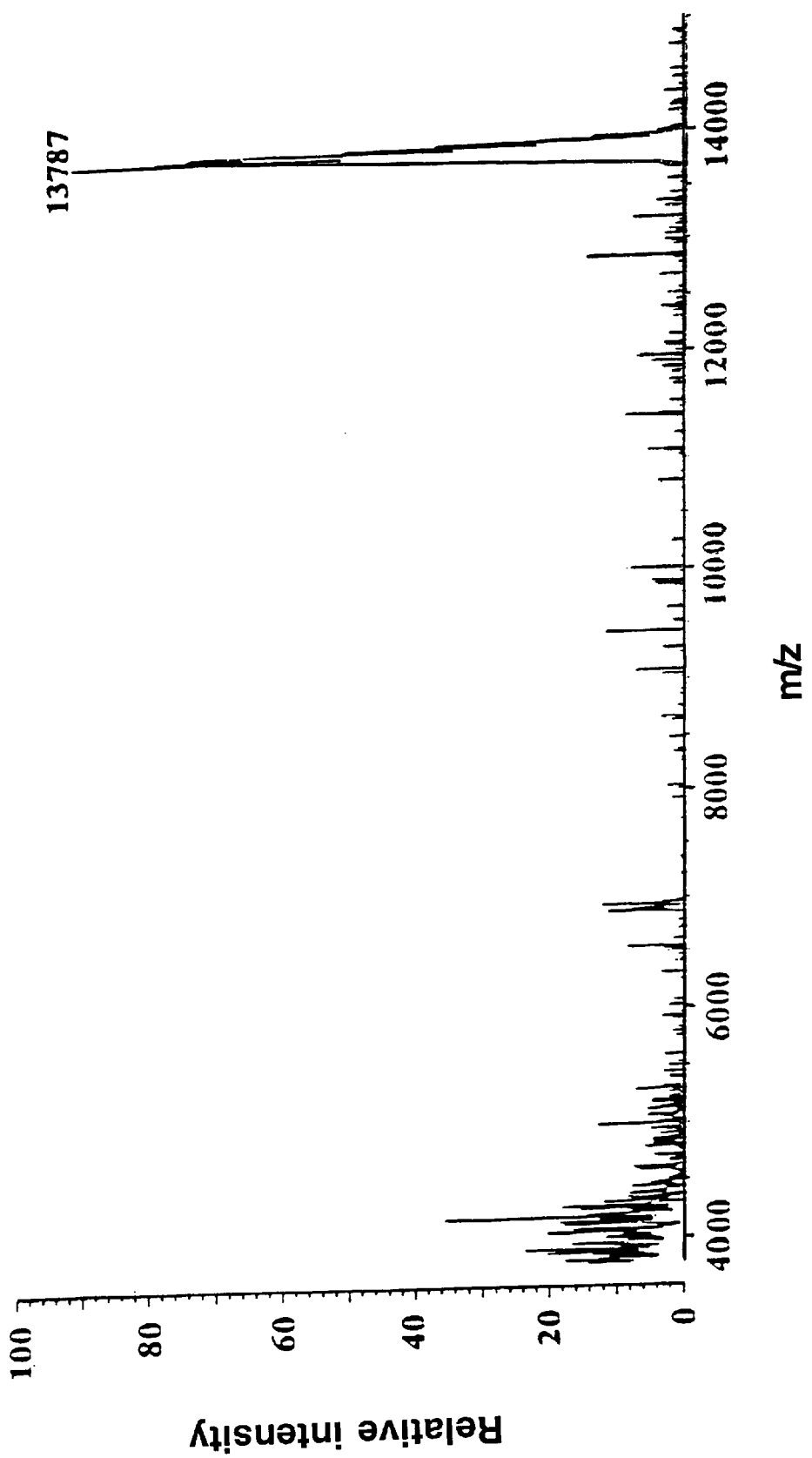
FIG. 3 shows the matrix-assisted laser desorption ionization mass spectrum of MS2 bacteriophage from crude culture broth with acetic acid and α-cyano-4-hydroxycinnamic acid matrix.

Spectra of crude MS2 cultures did not require higher laser intensity to observe the coat protein molecular ion; however, the resolution was poorer than spectra obtained from semi-purified preparations (FIG. 3). Conservation of the coat protein sequence means that mass difference from the calculated molecular weight value of 13729 Da is due to natriation or kalionation. Spectra were obtained with several matrices; however, spectral quality varied from sample to sample of the crude phage solution. In addition, phosphatidylethanolamine from the host *E.coli* cell walls were observed with certain MALDI matrices.

EXAMPLE 6
Detection of Tobacco Mosaic Virus

Figure 4:
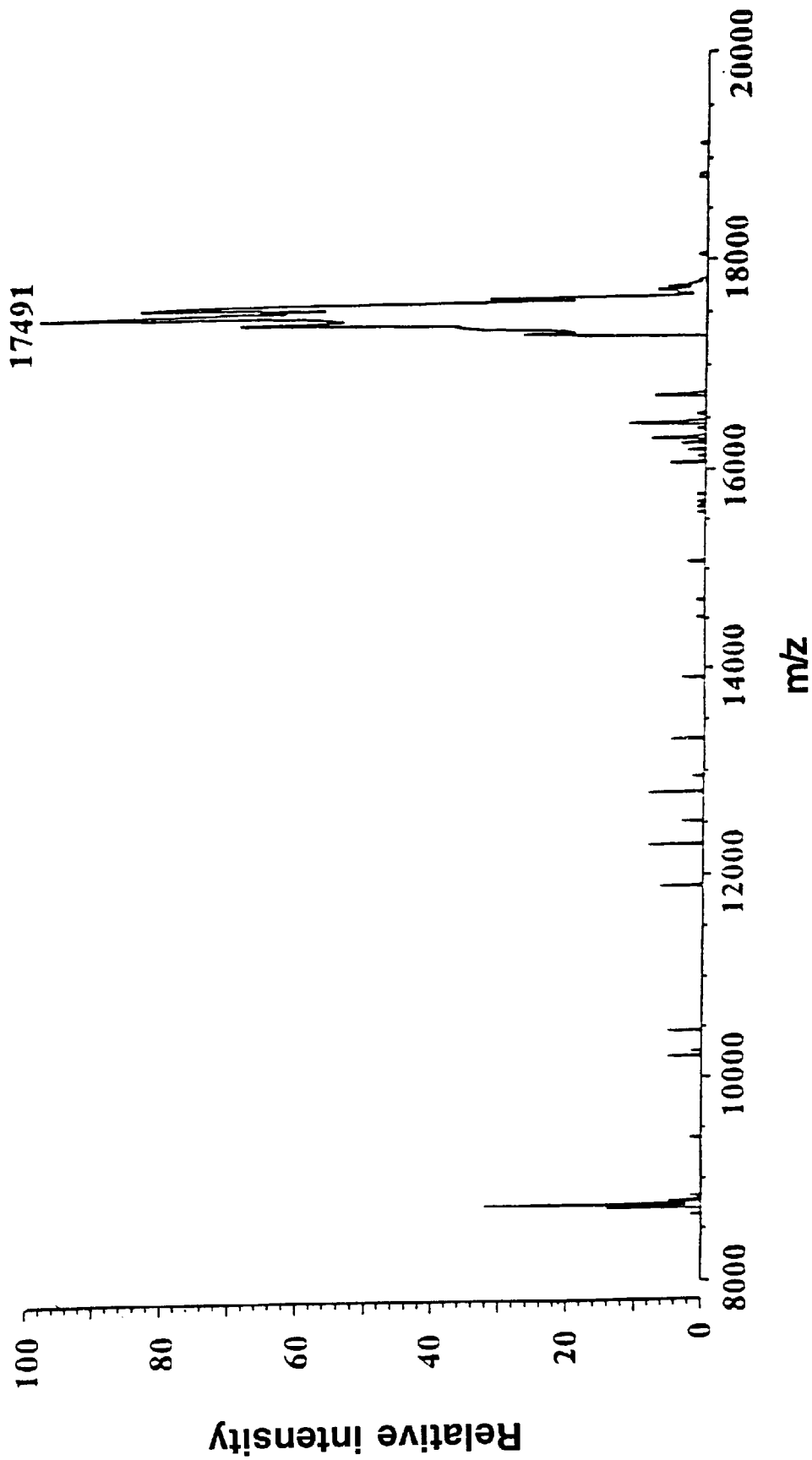
FIG. 4 shows the matrix-assisted laser desorption ionization mass spectrum of tobacco mosaic virus directly from a piece of an infected leaf. 2M citric acid and sinapinic acid matrix were applied to the infected leaf piece prior to desorption.

The desorption of the tobacco mosaic virus from a tobacco leaf presented the challenge of a host that could potentially inhibit desorption of the protein of interest with the MALDI matrix, and that contains an excess of molecules that could suppress MALDI detection. Despite these complications, FIG. 4 demonstrates the detection of the tobacco mosaic virus directly from a leaf and a leaf extract sample. The extract provided more intense (i.e. as much as 10× ion current) detection of the TMV virus compared to direct detection from a leaf piece.

On the basis of the published complete nucleotide sequence of the genomic RNA of the U2 strain of TMV, the expected mass for the coat protein is 17,459 Da (21). The mass difference may be attributed to mutations or salt adducts. Table 1 demonstrates the mass accuracy from a MALDI-TOF instrument, to which the manufacturer attests a 0.1% mass accuracy from standards. The addition of citric acid to infected leaf pieces provided more facile detection of TMV than acetic acid. Dissociation of TMV coat proteins has been associated with the disruption of carboxylate groups a t subunit interfaces (22).

TABLE 1

Molecular Masses for Viral Proteins Measured without Isolation

| Phage or virus | Number of expected capsid protein (molecules/virion) | Molecular expected (m/z) | masses observed[a] (m/z) | Mass accuracy (%) |
|---|---|---|---|---|
| MS2 bacteriophage | 180 | 13729 | 13784 ± 6[b] | 0.40 |
| Tobacco mosaic virus | 2130 | 17461 | 17464 ± 29 | 0.02 |
| Venezuelan equine encephalitis | 240 | 30941 | 31225 ± 105 | 0.92 |

[a]average molecular mass;
[b]n = 3

EXAMPLE 7
Detection of Venezuelan Equine Encephalitis Virus.

Figure 5:
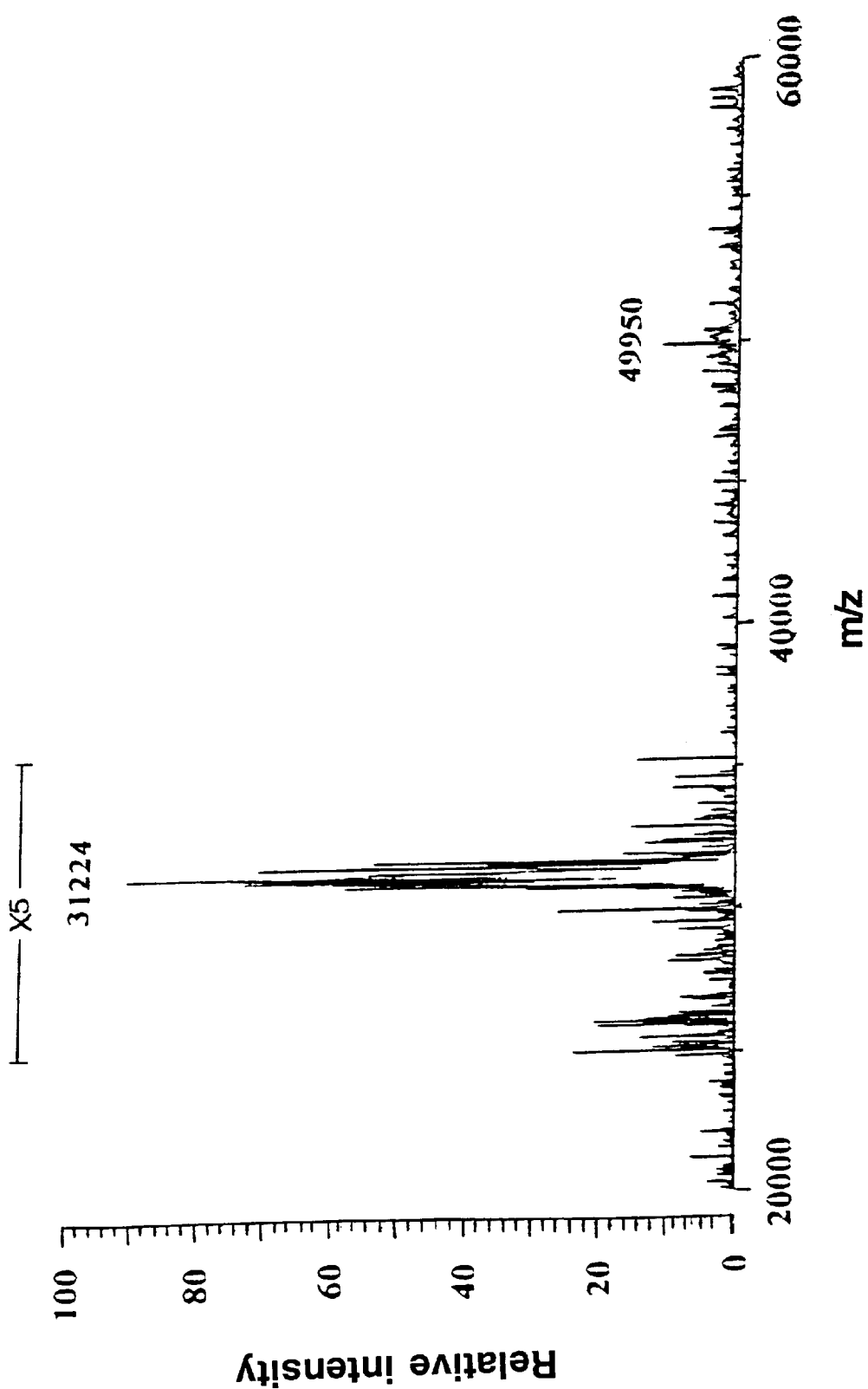
FIG. 5 shows MALDI mass spectrum of sucrose gradient purified Venezuelan equine encephalitis with acetic acid and sinapinic acid matrix.

From the semi-purified preparation of Venezuelan Equine Encephalitis, FIG. 5 displays the mass spectrum of the nucleocapsid protein and an indication of the less glycosylated glycoprotein of the two transmembrane glycoproteins (E1 and E2). This virus sample is representative of a biological virus preparation, which contains chemicals known to degrade matrix-assisted laser desorption ionization spectra. Maximum laser intensity was needed to observe the VEE capsid protein. While the capsid protein peak is clearly visible at m/z 31220, the peak associated with the E1 glycoprotein at m/z 49950 is observed at a 2:1 signal to noise ratio. Peak suppression in UV-MALDI analysis of glycoproteins is a frequent encountered problem due to properties of the sugar moiety.

Discussion

The present invention demonstrates that UV-MALDI can be used to rapidly detect characteristic proteins of viruses and bacteriophages. Without pre-concentration and little or no purification, bacteriophage MS2, tobacco mosaic virus, and Venezuelan equine encephalitis virus have been detected from a variety of biological media within 3 minutes. Certain matrices and additives increase the probability of observing viral proteins; however, this does not limit the usefulness of this technique.

While MALDI mass spectrometry has been gaining popularity as an analytical technique for a range of pure compounds, application of the MALDI mass spectrometry to samples in biological media will expand the utilization of this technique. The concepts applied in the present invention may be utilized for the rapid screening of more complex viruses that contain a diverse number of proteins.

The following references are cited herein.

(1) Ember, L. R. C & E News 1996.
(2) Karas, M., et al., Anal. Chem. 1988, 60: 2299–2301.
(3) Jespersen, S., et al., J. Rapid Commun. Mass Spectrom. 1994, 8: 58 1–584.
(4) Beavis, R., et al., Proc. Natl. Acad. Sci., USA 1990, 87: 6873–6877.
(5) C. Petersen, J., et al., J. Virology 1974, 14: 740–744.
(6) Kinney, R., et al., Virology 1989, 170: 19–30.
(7) Grieder, F., et al., Virology 1995, 206: 994–1006.
(8) Despeyroux, D., et al., J. Rapid Commun. Mass Spectrom. 1996, 10: 937–941.
(9) Davis, J., et al., J. Mol. Biol. 1963, 6: 203–207.
(10) Walkey, D. Applied Plant Virology; John Wiley & Sons, Inc.: New York, 1985.
(11) Kussman, M., et al., J. Mass Spectrom. 1997, 32: 593–601.

(12) Worrall, T. A., et al., Anal Chem. 1998, 70: 750–756.
(13) Buzzell, A. J. Am. Chem. Soc. 1960, 82: 1636–1641.
(14) Blowers, L. E., et al., J. Gen. Virol. 1982, 61: 137–141.
(15) Fraenkel-Conrat, H. Virology 1957, 4: 1–4.
(16) Ohno, T., et al., Virology 1977, 76: 429–432.
(17) Wilson, T. M., et al., FEBS Letters 1976, 64: 285–289.
(18) Bornsen, K., et al. Rapid Commun. Mass Spectrom. 1997, 11: 603–609.
(19) Bergman, A., et al., FEBS letters 1996, 397: 45–49.
(20) Walker, K. L., et al., Anal. Chem. 1995, 67: 4197–4204.
(21) Solis, I., et al., Virology 1990, 177: 553–558.
(22) Culver, J. N., et al. Virology 1995, 206: 724–730.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of detecting viral proteins from a complex environment, comprising the steps of:
   preparing a crude sample of said environment;
   adding an organic acid to said sample independently; and
   detecting viral proteins by utilizing mass spectrometry to said sample.

2. The method of claim 1, wherein said viral proteins are structural proteins.

3. The method of claim 2, wherein said viral protein is a capsid protein.

4. The method of claim 1, wherein said crude sample is selected from the group consisting of semi-purified and non-purified preparations.

5. The method of claim 1, wherein said organic acid is selected from the group consisting of acetic acid and citric acid.

6. The method of claim 1, wherein said detection is accomplished in less than 3 minutes.

7. The method of claim 1, wherein a femtomolar concentration of said viral protein is detected.

8. The method of claim 1, wherein said protein detected is a bacteriophage protein.

9. The method of claim 1, wherein said mass spectrometry is selected from the group consisting of fast atom bombardment mass spectrometry, plasma desorption mass spectrometry, laser desorption mass spectrometry, matrix-assisted laser desorption ionization time-of-flight mass spectrometry and electrospray mass spectrometry.

* * * * *